United States Patent [19]

Shevrin et al.

[11] Patent Number: 4,699,153
[45] Date of Patent: Oct. 13, 1987

[54] SYSTEM FOR ASSESSING VERBAL PSYCHOBIOLOGICAL CORRELATES

[75] Inventors: Howard Shevrin; William J. Williams; Robert E. Marshall, all of Ann Arbor, Mich.

[73] Assignee: The University of Michigan, Ann Arbor, Mich.

[21] Appl. No.: 726,056
[22] Filed: Apr. 23, 1985
[51] Int. Cl.[4] ............................................. A61B 5/04
[52] U.S. Cl. ................................... 128/731; 128/745
[58] Field of Search ............................ 128/731–732, 128/733, 745

[56] References Cited

PUBLICATIONS

Williams et al.; "A Transinformation Measure of Word Meaning in Evoked Potentials"; 4-1984.
Shevrin; "Unconscious Conflict: A Convergent Psychodynamic and Electrophysiological Approach"; Emotional & Cognitive Factors in Unconscious Processes, Stanford, Calif., 7-1984.
Boudrot et al.; "A Clinical Feedback EEG System"; Am. J. EEG Technol., No. 3, 9-1976, pp. 117-127.
"A Continuous Information Theoretic Approach . . . ", by Fuller and Williams, Biological Cybernetics, Jun. 20, 1982.
"Cortical Response to Tactile Stimulus . . . ", by Shevrin and Rennick, Psychophysiology, vol. 3, No. 4, 1967.
"Visual Evoked Response Correlates . . . ", by Shevrin and Fritzler, Science, vol. 161, pp. 295-298, Jul. 19, 1968.
"Brain Response Correlates of Repressiveness", by Shevrin and Fritzler, Psychological Reports, 1968, 887-92, 12/68.
"Repressiveness as a Factor in the Subliminal . . . ", by Shevrin, Smith, and Fritzler, The Journal of Nervous and Mental Disease, vol. 149, No. 3, 1969.
Published comments of Dr. Shevrin, Psychological Variables in AEP Experiment (Average Evoked Potentials).
"Subliminally Stimulated Brain and Verbal Responses . . . ", by Shevrin and Smith, Journal of Abnormal Psychology, 1970, vol. 75, No. 1, 39-46.
"Direct Measurement of Unconscious Mental Processes: . . . ", by Shevrin, Smith, and Hoobler, Proceedings, 78th Annual Convention, APA 1970.
"Average Evoked Response and Verbal Correlates . . . ", by Shevrin and Smith, Psychophysiology, vol. 8, No. 2, 1971.
"Brain Wave Correlates of Subliminal Stimulation . . . ", by Shevrin, Psychological Issues Monograph 30, Psychoanalytic Research, vol. III, No. 2, 1973.
"Neurophysiological Correlates of Psychodynamic Unconscious Processes", by Shevrin, Symposium on the Unconscious under the auspices of the Georgian Academy of Sciences, Tbilisi, USSR, 1978.
"Evoked Potential Evidence for Unconscious Mental Processes: A Review of the Literature", by Shevrin, International Symposium on the Unconscious, Tsibili, Georgia, USSR, 1978.
"Some Assumptions of Psychoanalytic Communication: . . . ", by Shevrin, Communicative Structures and Psychic Structures, 1977.
"Glimpses of the Unconscious", by Shevrin, Psychology Today, Apr. 1980.

Primary Examiner—Kyle L. Howell
Assistant Examiner—Angela D. Sykes
Attorney, Agent, or Firm—Rohm & Monsanto

[57] ABSTRACT

A system for assessing psychobiological conditions of a subject utilizes a plurality of words which are selected to be in four categories as critical stimuli. The words are presented by a tachistoscope to the subject in subliminal and supraliminal modes of operation. Subliminal stimulation of the subject is achieved by presenting the selected words for an exposure period of approximately one millisecond. The supraliminal exposure time is approximately thirty milliseconds. Prior to stimulation, the subject is diagnosed in accordance with conventional psychoanalytical techniques to establish the presence and nature of a pathological condition. The words are selected and categorized in four groups: pleasant words, unpleasant words, words related to a diagnosed conscious pathological condition, and words related to a diagnosed unconscious pathological condition. The brain wave responses which are evoked by the stimulation are collected via electrodes and analyzed in accordance with a transinformation technique which is based on information signal theory for establishing a probabilistic value which corresponds to the information content of the evoked responses.

23 Claims, 4 Drawing Figures

SYSTEM FOR ASSESSING VERBAL PSYCHOBIOLOGICAL CORRELATES

BACKGROUND OF THE INVENTION

This invention relates generally to systems for examining brain wave responses to stimulation of a subject, and more particularly to a system wherein evoked potentials responsive to selected critical verbal stimuli are analyzed mathematically to establish a probabilistic value corresponding to the information content of the evoked signal responses.

It has long been proposed that the unconscious mind is psychologically meaningful in that there exists a psychic continuity whereby seemingly discontinuous psychological patterns are actually continuous, but certain psychological events are unknown and in the unconscious. It has therefore been reasoned that the existence of an unconscious must be assumed in psychoanalysis, but methods other than the clinical methods of psychoanalysis must be employed to demonstrate the unconscious. The experimental stimulus used in some experimental efforts to demonstrate the unconscious is a picture of a pen pointing at a knee. By tracing the conceptual associations of pen and knee, by words such as "ink," "paper," "foot," and "leg," rational, secondary process thinking was sampled. However, if clang associations were to be traced, then the experiment would be sampling primary process ideation. Examples of such clangs would be "pennant pennant," "happen," "neither," and "any." Finally, two clangs can combine or condense to form a new word, "penny,"which is entirely unrelated in meaning to its components. Associations to this clang condensation can be traced in the form of words such as "coin," "nickel," "Lincoln," etc. The penny combination is another level of primary-process ideation based on the fact that the stimulus is a pictorial representation of a word, or a rebus, one of the oldest forms of writing and closely allied to dream thinking. Aside from the theoretical relevance of the stimulus, it has the technical advantage of involving no clinical judgment in scoring. Lists of associations based on normative data can be used by assistants with an error rate which is consistently less than 3%.

The rebus method of analysis has been used successfully in various studies. For example, in one experiment, it was shown that pen and knee clang associations and penny rebus associations appeared more often in associations following Stage I, rapid eye movement awakenings, than after Stage II awakenings. On the other hand, pen and knee conceptual associations appeared more frequently following Stage II awakenings than after Stage I, rapid eye movement awakenings. Primary process thought was prominent following dream arousals and secondary-process thought was prominent following one type of non-dream arousal.

It was not, however, until the rebus method was combined with the method of average evoked responses that it became possible to detect directly brain responses to subliminal stimuli and to discover the usefulness of these waves as indicators of complex dynamic and cognitive processes. The average evoked response is based upon the sampling of short periods of the EEG immediately following a given stiumlus. Ordinarily, it is difficult to detect a specific stimulus-locked response in the EEG beacause the EEG reflects so many other simultaneous responses to internal and external stimuli. However, by repeatedly sampling the EEG, a pattern emerges which is directly related to a selected stimulus. It has now been shown that EEG amplitudes within the first 300 milliseconds after stimulation are associated with attention.

In one well known experiment, it was postulated that attentional and perceptual processes were subliminal. This could be tested by presenting two matched stimuli, one of which could be more interesting than the other, and to predict that the more interesting stimulus would elicit a larger brain response. Thus, a matched pair of stimuli were presented in a series of experiments. The experimental stimulus was the fountain pen pointing at a knee, while a controlled stimulus, which matches the experimental one in size, configuration, color, and contour, lacks conventional meaning. FIG. 1A is the experimental stimulus and is a picture of a fountain pen pointed at a leg which is prominently flexed at the knee. FIG. 1B is the control stimulus which is made up of two nonsense figures matching the experimental stimulus in configuration, shape, color, and contour. It was found that one millisecond of exposure of the stimuli to a subject resulted in consistent discrimination between the two stimuli in favor of the rebus. Such discrimination took the form of a larger amplitude in the brain wave with a latentcy of approximately 170 milliseconds.

FIG. 2 is a schematic representation of an averaging method of an EEG signal for the same time epoch. As shown, each response appears different from the other. However, if the different segments are added algebraically, then a consistency emerges reflected in a sizable amplitude. The average evoked response curve shows the appearance of this amplitude. This curve is a total algebraic sum for the amplitude increment, which is then divided by the total number of responses to give the averages.

It therefore has been established by experimentation that a brain wave in the form of an average evoked response discriminates between two subliminal stimuli. Such discrimination is attributable to an amplitude component associated with attention which occurs at approximately between 140 and 80 milliseconds post-stimulus; less than a quarter of a second. Associations to the subliminal rebus stimulus are activated and can be elicited by a free association method. Such free association confirms that thought processes are activated by a subliminal stimulus and persist unconsciously. During such association, the subject is totally unaware of associating more of one category of words than another. The conceptual, secondary-process associations, such as the knee associations, are positively correlated with the size of the discriminating average evoked response amplitude. In other words, the larger the average evoked response amplitude to the rebus stimulation, the more frequently will conceptual secondary-process associations be elicited. This relationship establishes a link between a truly neurophysiological event and an unconscious thought process, for the subjects can in no way be aware of this relationship. However, primary-process associations (clang and rebus words) are not correlated with this amplitude component. Rather, the incidence of primary-process associations is contingent upon the appearance of bursts of rhythmic activity in the alpha range.

Repressiveness, as rated independently on the Rorschach test, is negatively correlated with the magnitude of the discriminating amplitude for the subliminal stimuli. Thus, the more repressive the person is judged on the Rorschach, the smaller will be the average evoked response amplitude in response to the subliminal rebus stimulus. However, when the same stimulus is supraliminal, there is a tendency for the highly repressive person to respond with a larger amplitude. Thus, the highly repressive person responds differently to the same stimulus depending upon whether or not it is subliminal or supraliminal. Additionally, the more repressive the person is, the fewer stimulus-related associations, of all kinds, primary and secondary process, the person will use in free association.

It is a problem with the known methods of analyzing and interpreting average evoked potentials that the information is obtained generally visually by determining the amplitudes of the peaks and their temporal locations in the post-stimulus epoch. There is a need for a system of analysis wherein greater amounts of information can be extracted from the evoked potentials.

SUMMARY OF THE INVENTION

The amount and quality of information which is available from evoked potentials obtained from a subject's scalp are improved by this invention which provides a method of assessing psychobiological responses to verbal stimuli. In accordance with the invention, a plurality of verbal inputs in the form of respective groups of words are selected, each such group having a respective categorical aspect. A first group of the words may have a pleasant connotation; a second group of the words may have an unpleasant connotation; and third and fourth groups of words may have connotations which are related to diagnosed conscious and unconscious pathological conditions, respectively, of the subject. The subject is stimulated subliminally by presenting the words to the subject for an exposure period which is insufficient to cause conscious awareness. The subject is additionally supraliminally stimulated by presenting the words for a longer period of time. The evoked potentials are collected and analyzed mathematically using a transinformation technique which produces a probabilistic value which corresponds to the amount of information in the evoked response signals.

Subliminal stimulation is achieved by presenting the words on a tachistoscope for an exposure period of approximately one millisecond. The supraliminal stimulation is achieved by extending the period of exposure to approximately thirty milliseconds.

Conventional psychoanalytical techniques are used to diagnose a psychopathic condition of the subject. At least certain ones of the words, particularly those related to the conscious and unconscious pathological situations of the subject, are selected in response to the diagnosis.

In accordance with an apparatus aspect of the invention, an arrangement for assessing psychobiological responses of the subject to verbal stimulus is provided with a presentation device for presenting verbal stimuli to the subject. The presentation means, which may be a tachistoscope, is operable in subliminal and supraliminal modes. A plurality of electrodes are arranged in electrical communication with the subject so as to provide at a terminal thereof the brain wave signals, in a known manner. Additionally, a system for analyzing the electrical signals is arranged to analyze from a probabilistic standpoint the electric signals in accordance with a transinformation technique for determining the amount of information in the electrical signals. The use of an information theoretic approach to determining the information content of the evoked responses provides the significant advantage that analysis can be achieved without the need for large numbers of repetitions of the presentation of the stimuli. Thus, the deleterious effects of large numbers of repetitions can be avoided by use of the present invention.

INCORPORATION BY REFERENCE

Applicants incorporate herein by reference, in their entirety, an article entitled "Unconscious Conflict: A Convergent Psychodynamic and Electrophysiological Approach" by Howard Shevrin, based on a presentation at a workshop entitled *Emotional and Cognitive Factors in Unconscious Processes*, at The Center for Advanced Study in the Behavioral Sciences, Stanford, California, July 5-9, 1984, and an article entitled "A Transinformation Measure of Word Meaning In Evoked Potentials" by W. J. Williams, H. Shevrin, and R. E. Marshall, Apr. 25, 1984.

BREIF DESCRIPTION OF THE DRAWINGS

Comprehension is facilitated by reading the following detailed description in conjunction with the annexed drawing, in which.

DETAILED DESCRIPTION OF THE INVENTION

The system for performing a psychobiological assessment of conscious and unconscious correlates of psychiatric symptoms, in accordance with the present invention, begins with a patient interview, which will generally lead to subsequent patient interviews, wherein psychodiagnostic tests are performed. Such testing is performed in accordance with established psychoanalytical techniques for the purpose of determining whether a psychopathic situation is present in the subject. Preferably, such an analysis is performed by a clinical team. It is to be understood that, for present purposes, which are largely experimental, subjects having psychoanalytically establishable pathologic conditions are preferred to establish a barometer against which the experimental results can be judged. However, such a clinical diagnosis is not an element of the invention. Subjects suffering from phobias and pathological grief reactions generally have clear-cut complaints which could become the focus of the experiment. Other subjects, however, might also prove suitable. These include anorectics and subjects with panic disorders, conversion reactions, et cetera. For purposes of selecting the subjects, the diagnostic evaluation consisted of three or four unstructured, psychodynamic interviews, an unstructured psychiatric interview directed toward identifying any medical or biological psychiatric disorders, and a battery of psychodiagnostic tests, such as WAIS, Rorschach, TAT, and Early Memories.

The second phase in establishing the experimental system consists of selecting a plurality of words which are related to the patient's experience of symptoms and underlying emotional causes. In one experimental situation, two categories of the subject's own words were selected from the interview and test protocols. A first category related to the subject's experience of the complaint (conscious words), and the other category related to the inferred unconscious conflict (unconscious words). Eight words in each category were finally selected by consensus. Additionally, two further categories of eight words each were added for control purposes. These included pleasant words and unpleasant words selected from the known Osgood lists. The pleasant words serve as a control for unpleasantness, since the other three categories were all composed of unpleasant words. However, the words in the unpleasant category served as a control for the two pathologically related unpleasant word categories.

Figure 1A:
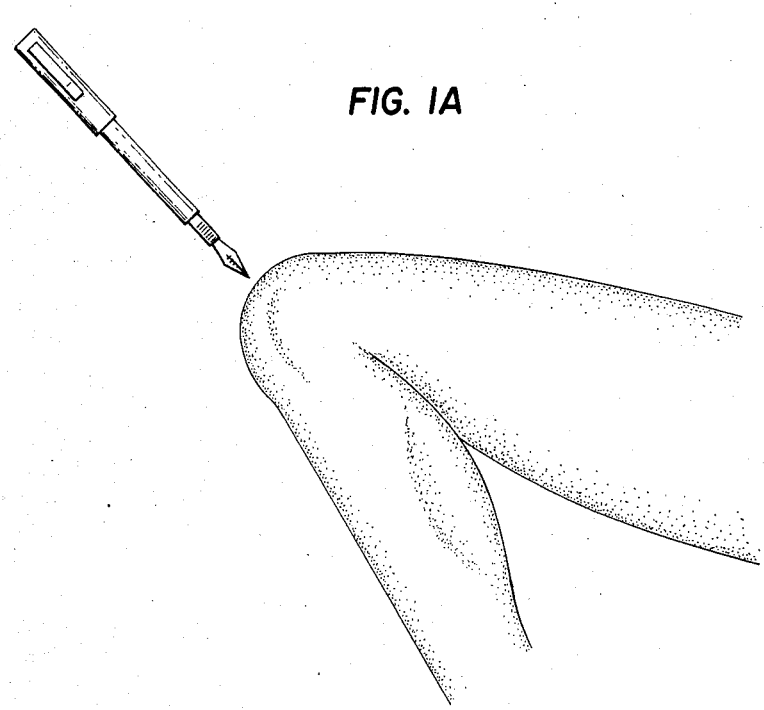
FIG. 1A is a representation of a meaningful stimulus showing a fountain pen pointed at a knee.
Figure 1B:
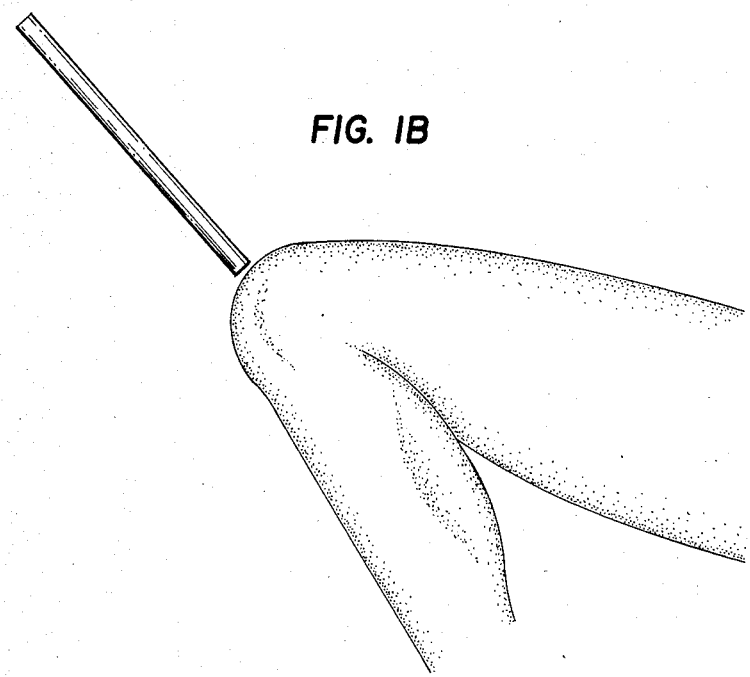
FIG. 1B is a representation of a meaningless stimulus having a general appearance similar to that of the meaningful stimulus.
Figure 2:
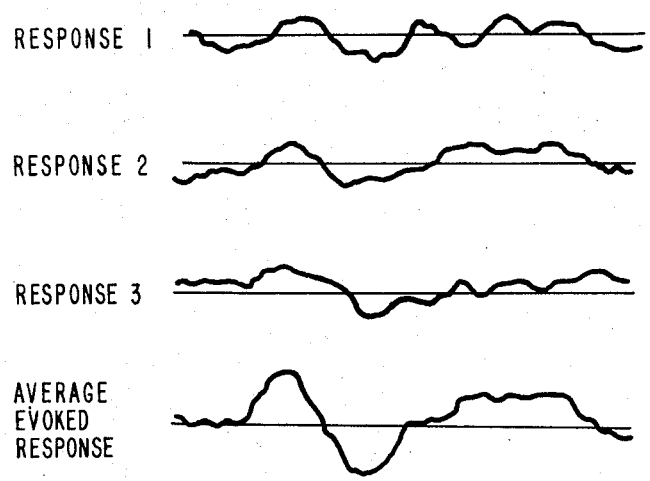
FIG. 2 is a representation of evoked response signals showing the manner in which they are averaged to produce an average evoked response signal.
Figure 3:
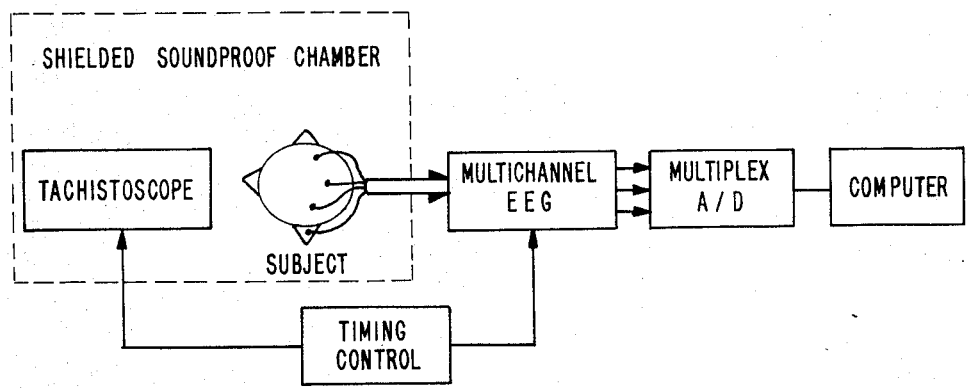
FIG. 3 is a schematic representation of a system for stimulating a subject and analyzing a response using a computer system.

FIG. 3 is a schematic representation of a system which is suitable for the practice of the invention. As shown in this figure, a commercially available tachistoscope and the subject are placed in a shielded soundproof chamber. The subject is connected by a plurality of electrodes to a multichannel EEG machine, also commercially available. The output of the EEG machine is coupled to a multiplexing analog-to-digital converter which subsequently feeds a multiplex digital signal to a computer system. Timing of the tachistoscope is governed by a timing control system which synchronizes the tachistoscope and the EEG machine. It is to be understood that the arrangement of elements shown in FIG. 3 is merely illustrative of a system suitable for practicing the invention, and that various other arrangements using different components may be utilized. For example, the tachistoscope may be replaced with a computer display or some other display device. Also, such a display device may be controlled by the computer.

After the subject has been wired to the system, the 32 words are flashed in the tachistoscope at subliminal and supraliminal exposure rates. A subliminal exposure may illustratively be on the order of one millisecond, and is sufficiently fast that the subject remains unaware, at the conscious level, of the stimulation. Subsequently, the words are flashed supraliminally so that the subject attains a conscious awareness. A supraliminal exposure may be on the order of 30 milliseconds.

After each stimulation, the resulting collection of evoked responses to the selected words is entered tachistoscopically and evaluated utilizing information-theoretic analysis in the computer. In accordance with the invention, the method of analysis utilizes a transinformation model. Transinformation refers to the amount of information over an information channel from an information source to an information output on the receiving end. For example, a person speaking into a telephone may be viewed as an information source. What is actually heard on the other end is the information output. Since information generally is lost in transmission, the amount of transinformation is always less than the total amount of information at the source. In the present situation, the information source is the word presented in a tachistoscope, and the information output is the evoked response potential at the electrode. The question to be answered by the transinformation analysis is how much of the information present in the word having to do with its category membership, e.g. conscious, unconscious, pleasant, and unpleasant, is present in the evoked response potential. Transinformational analysis is rooted in information theory and is based on the concept of a binary communication channel. If the set of stimulus symbols is called x and the set of response signals is called y, then transinformation may be defined to be $$I(x; y) = H(x) - H(x/y)$$

where $H(x)$ is the entropy, and can be considered to be the average amount of selfinformation in the scheme, and $H(x/y)$, which corresponds to the equivocation entropy, is:

$$H(x/y) = \Sigma_i \Sigma_j P(x_i/y_j)[Log_2 P(x_i/y_j)] P(y_j)$$

For example, suppose there are two input stimuli $x_1$ and $x_2$, and two output responses $y_1$ and $y_2$. If the following probabilities are assumed;

$$P(x_1) = 0.5, P(x_1/y_1) = 1, P(x_2/y_1) = 0$$

$$P(x_2) = 0.5, P(x_2/y_2) = 1, P(x_1/y_2) = 0$$

$$P(y_1) = 0.5, P(y_2) = 0.5$$

then $$I(x; y) = -0.5 \, Log_2(0.5) - 0.5 \, Log_2(0.5) -$$
$$[1 \cdot Log_2(1)] \cdot 0.5 - [0 \cdot Log_2(0)] \cdot 0.5 -$$
$$[0 \cdot Log_2(0)] \cdot 0.5 - [1 \cdot Log_2(1)] \cdot 0.5 = 1 \text{ bit}$$

where a bit is a unit of information associated with the selection of one of two likely events ($P_k = 0.5$).

An essential aspect of the methodology of word-response testing is the selection of words used as stimuli. The selected words should "belong" in some sense to the four categories of interest, i.e., words related to the conscious or unconscious pathology and words possessing pleasant and unpleasant connotations. It is also important to provide a framework for the process itself, to afford the team of clinicians a readily interpretable set of metrics to indicate convergence or divergence of opinion and, at the same time, allow the assessment of relative degrees of belonging and non-belonging to the categories of interest. It is also desirable to indicate the joint properties of words. For example, a word may be considered to be "unpleasant" and also highly relevant to "conscious" pathology.

These considerations have led to a technique of quantifying the various aspects of this process. "Belonging" is quantified for each word in terms of each of four categories on a scale ranging from +10 to −10. This scale constitutes a multivariate metric space in which the orthogonal axes are the measures of "belonging" for each category. In this manner, the joint properties, as well as the individual properties, of the words may be analyzed. These rankings may also be thought of as measures of "belief" and "disbelief" in known psychoanalytical processes.

The process of reviewing the word weightings is an interaction among the members of the team of clinicians. Such a process has been formalized as a Delphi procedure in which some or all of the developing opinions are made available to a team as the process continues through several iterations. Problems which may arise and premises for such procedures are discussed amongst the team. Although raw scores for all iterations can be employed by the team to obtain rankings and discover inconsistencies, a metric appears desirable for this purpose.

The development of a single metric to express all relevant properties of the selection process is desirable, but may not be realistic. Properties of interest in word selection are several, but not easily confined in a single meaningful metric. An important property is closeness to an ideal category. This implies a distance metric as readily expressed as a Euclidian distance of the multivariate word ranking to the ideal ranking, i.e., a ranking of +10, −10, −10, and +10, for a four-category space. Coupled to this property is a distance from other categories. Combining these two distances in a single function serves to provide a meaningful measure of "closeness" to the ideal ranking and "distance" from other categories. In other words, it is a combined or simultaneous measure of "belonging" and lack of ambiguity.

In accordance with the invention, a most promising measure among many available seems to be the mean square distance of the distance metric, and a form of likelihood ratio for the function. A promising function is a product of distance to ideal category and the sum of inverse distances to other categories.

Another property of interest is the convergence or divergence of opinion during the selection process. This may best be expressed as the sequence of variances for each iteration of the ranking process. This technique is employed in Delphi procedures. Should a variance sequence prove divergent, for example, the word should probably be rejected as ambiguous or poorly defined.

Another property relates to the inter-category distance structure. It may be desirable to include an explicit evolution of the compactness of the set of category words and separation of the overall category sets. It is to be understood, however, that a certain amount of overlap among the above-described functions exists, and in certain selection processes, such quantifying properties may be difficult to combine. Nevertheless, a multivariate metric space quantifying system is suited to the process of word selection and makes available a well-developed statistical methodology for analysis.

Although the invention has been described in terms of specific embodiments and applications, persons skilled in the art can, in light of this teaching, generate additional embodiments without exceeding the scope or departing from the spirit of the claimed invention. Accordingly, it is to be understood that the drawing and descriptions in this disclosure are proffered to facilitate comprehension of the invention and should not be construed to limit the scope thereof.

What is claimed is:

1. A method of assessing psychobiological responses to verbal stimuli, the responses being in the form of evoked potentials obtained from a subject's scalp, the method comprising the steps of:
   selecting a first verbal input formed of a first group of words, each group having a pleasant connotation;
   selecting a second verbal input formed of a second group of words, each word having an unpleasant connotation;
   selecting a third verbal input formed of a third group of words, each word having a connotation relating to a diagnosed conscious pathological condition of the subject;
   selecting a fourth verbal input formed of a fourth group of words, each word having a connotation related to a diagnosed unconscious pathological condition of the subject;
   subliminally stimulating the subject using at least selected ones said first, second, third, and fourth groups of words;
   supraliminally stimulating the subject using at least selected ones of said first, second, third, and fourth groups of words;
   collecting the responses resulting from said steps of subliminally stimulating and supraliminally stimulating; and
   analyzing mathematically said collected responses using transinformation techniques for producing at least one probabilistic value corresponding to an amount of information in the responses.

2. The method of claim 1 wherein said step of subliminally stimulating comprises the step of presenting said words on a tachistoscope for a period of approximately one millisecond 3. The method of claim 1 wherein said step of supraliminally stimulating comprises the step of presenting said words on a tachistoscope for a period of approximately thirty milliseconds.

4. The method of claim 1 further comprising the step of diagnosing a psychological condition of the subject.

5. The method of claim 4 wherein said steps of selecting said third and fourth verbal inputs are performed in response to said step of diagnosing.

6. The method of claim 1 wherein said step of analyzing mathematically comprises the further step of averaging a plurality of the responses algebraically.

7. The method of claim 1 wherein said step of collecting further comprises the step of recording the responses on a recorder.

8. An arrangement for assessing psychobiological responses of a subject to verbal stimuli, the arrangement comprising:
   presentation means for presenting verbal stimuli in the form of written words selected from predetermined categories of meaning to the subject, said presentation means being operable in subliminal and supraliminal modes;
   electrode means for communicating electrically with the subject and providing an electrical signal responsive to brain wave activity of the subject;
   control means for controlling a timing of said presentation means; and
   analysis means for analyzing said electrical signal probabilistically in accordance with a transinformation technique whereby an amount of information in said electrical signal responsive to said predetermined categories of said written words is determined.

9. The arrangement of claim 8 wherein said presentation means comprises tachistoscope means having at least one field for presenting said verbal stimuli.

10. The arrangement of claim 9 wherein said tachistoscope means is operable in said subliminal mode corresponding to exposure for a period of approximately one millisecond.

11. The arrangement of claim 9 wherein said tachistoscope means is operable in said supraliminal mode corresponding to an exposure of approximately thirty milliseconds.

12. The arrangement of claim 8 wherein there is further provided sound proof chamber means for accommodating the subject and said presentation means.

13. The arrangement of claim 8 wherein there is further provided analog-to-digital converter means for converting said electrical signal to a corresponding digital signal which is delivered to said analysis means.

14. The arrangement of claim 13 wherein said analysis means comprises digital computing means.

15. The arrangement of claim 8 wherein said electrode means comprises a plurality of electrode means for providing a corresponding plurality of electrical signals, there being further provided multiplex means for forming a composite signal.

16. The arrangement of claim 15 wherein there is further provided electroencephalograph means interposed between said plurality of electrode means and said multiplex means.

17. The method of claim 8 wherein there are provided a plurality of electrode means for providing respective electrical signals, there being further provided multiplex means for producing a composite signal.

18. A method of establishing the presence of a pathological situation in a patient, the method comprising the steps of:
    clinically diagnosing the patient's psychological condition using interviews to form a preliminary diagnosis;
    selecting a plurality of verbal stimuli in the form of words selected from predetermined categories of said words responsive to said step of clinically diagnosing;
    stimulating the patient subliminally and supraliminally using said verbal stimuli;
    converting evoked response potentials obtained from the patient into a digital signal; and
    analyzing said digital signal in a computing machine in accordance with a transinformation technique to obtain a value corresponding to the information content of said digital signal responsive to said words.

19. The method of claim 18 wherein said step of selecting comprises the further steps of:
    establishing a scale range for defining a measure of belonging for said verbal stimuli; and
    establishing a distance measure for determining a distance of said verbal stimuli from an ideal category.

20. The method of claim 19 wherein said distance is represented as a mean square distance value.

21. The method of claim 19 wherein a distance function is represented as a product of a distance to an ideal category, and a sum at inversed distances to other categories.

22. The method of claim 18 wherein said step of analyzing comprises the further steps of:
    dividing said verbal stimuli into plural categories corresponding to unpleasantness, and a category corresponding to pleasantness;
    computing a transinformational profile for each of said categories; and
    computing said transinformational profiles of said plural categories corresponding to unpleasantness against said transinformational profile of said category corresponding to pleasantness.

23. The method of claim 22 wherein said transinformational profile of each of said categories corresponds to an average of transinformational profiles for each verbal stimulus in said category.

* * * * *